(12) United States Patent
Palla-Venkata et al.

(10) Patent No.: US 8,642,529 B2
(45) Date of Patent: Feb. 4, 2014

(54) LIQUID LOW SURFACTANT COMPOSITIONS STRUCTURED WITH A FIBROUS POLYMER

(75) Inventors: Chandra Shekar Palla-Venkata, Hamden, CT (US); Yuntao Thomas Hu, Orange, CT (US); Martin Swanson Vethamuthu, Southbury, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 12/946,169

(22) Filed: Nov. 15, 2010

(65) Prior Publication Data
US 2012/0122998 A1    May 17, 2012

(51) Int. Cl.
*C11D 3/22* (2006.01)

(52) U.S. Cl.
USPC ............ 510/471; 510/151; 510/426; 510/473

(58) Field of Classification Search
USPC .................................. 510/151, 426, 471, 473
See application file for complete search history.

(56) References Cited

U.S. PATENT DOCUMENTS

| | | | |
|---|---|---|---|
| 3,723,325 A | 3/1973 | Parran, Jr. | |
| 4,374,702 A | 2/1983 | Turbak et al. | |
| 4,487,634 A | 12/1984 | Turbak et al. | |
| 4,565,647 A | 1/1986 | Llenado | |
| 4,863,565 A | 9/1989 | Johnson et al. | |
| 5,009,814 A | 4/1991 | Kelkenberg et al. | |
| 5,079,162 A | 1/1992 | Ben-Bassat et al. | |
| 5,144,021 A | 9/1992 | Arie et al. | |
| 5,207,826 A | 5/1993 | Westland et al. | |
| 5,389,279 A | 2/1995 | Au et al. | |
| 6,685,919 B2 * | 2/2004 | Leinen et al. .................. 424/49 |
| 6,967,027 B1 | 11/2005 | Heux et al. | |
| 7,776,807 B2 | 8/2010 | Canto et al. | |
| 2005/0119151 A1 * | 6/2005 | Mayer et al. ................. 510/476 |
| 2007/0027108 A1 | 2/2007 | Yang et al. | |
| 2007/0197779 A1 | 8/2007 | Yang et al. | |
| 2008/0108541 A1 | 5/2008 | Swazey | |
| 2008/0108714 A1 * | 5/2008 | Swazey et al. ................. 516/31 |
| 2008/0146485 A1 | 6/2008 | Swazey | |
| 2010/0009891 A1 * | 1/2010 | Canto et al. ................... 510/418 |
| 2010/0081601 A1 * | 4/2010 | Boutique et al. ............. 510/295 |
| 2011/0039744 A1 * | 2/2011 | Heath et al. .................. 510/121 |
| 2011/0206746 A1 * | 8/2011 | Hagar et al. .................. 424/401 |
| 2011/0257070 A1 * | 10/2011 | Caggioni et al. ............. 510/418 |

FOREIGN PATENT DOCUMENTS

| | | |
|---|---|---|
| WO | 2009/101545 | 8/2009 |
| WO | 2009/135765 | 11/2009 |

OTHER PUBLICATIONS

Co-pending Application for Applicant: Palla-Venkata et al.; U.S. Appl. No. 12/946,186, filed Nov. 15, 2010, entitled: Liquid Surfactant Compositions Structured with Fibrous Polymer and Further Comprising Citrus Fibers Having no Flow Instability or Shear Banding.
Hu et al., *Comparison Between Shear Banding and Shear Thinning in Entangled Micellar Solutions*. J. Rheol., 2008, 52(2); p. 379-400.
Hu et al., *Role of Electrostatic Interactions in Shear Banding of Entangled DNA Solutions*, Micromolecules, 2008, 41, p. 6618-6620.
PCT Intetnational Preliminary Report on Patentability, dated, Nov. 6, 2012.

* cited by examiner

*Primary Examiner* — Charles Boyer
(74) *Attorney, Agent, or Firm* — Ronald A. Koatz

(57) ABSTRACT

The invention relates to surfactant structured liquids structured with fibrous polymer and which additionally contain specific low molecular weight water soluble polymers to eliminate flow instability.

5 Claims, 2 Drawing Sheets

LIQUID LOW SURFACTANT COMPOSITIONS STRUCTURED WITH A FIBROUS POLYMER

FIELD OF THE INVENTION

The present invention relates to surfactant structured liquids structured with fibrous polymers (e.g., micro fibrous cellulose suspending polymers). In particular, it relates to such compositions which additionally comprise specific low molecular weight water soluble polymers (e.g., cellulose gums). The polymers are used to eliminate flow instability problems caused by zero or near zero shear stress rate slope (plotted on graph of shear rate on x axis versus stress on y axis) and seen when fibrous polymers alone are used.

BACKGROUND

Structured liquid surfactant personal care compositions are desirable. Such structured liquids can be used, for example, to suspend beads and/or other particles desirable in personal care compositions. Such particles can be used, for example, as abrasives, encapsulates (e.g., for delivering additional benefit agents), or to provide visual cues (e.g., optical particles).

Typically, particles may be suspended in liquid personal care compositions using a variety of structuring systems. These may include use of acrylate polymers, structuring gums (e.g., xanthan gum), starch, agar, hydroxyl alkyl cellulose etc. When large particles are suspended (e.g., polyethylene particles, guar beads), levels of polymer used is typically 1% or more.

It has previously been shown that when certain fibrous polymers (e.g., micro fibrous cellulose with large aspect ratios) are used as structurants, these may provide efficient suspending properties even at polymer levels as low as 0.1% (see U.S. Pat. No. 7,776,807 to Canto et al.; U.S. Publication No. 2008/0108541 to Swazey and U.S. Publication No. 2008/0146485 to Swazey). The fibrous polymers are believed to form spider-network like structures which efficiently trap the particles inside the network and thereby impart good suspending properties. The polymers provide excellent rheological properties and are salt tolerant, if salt is used in the formulation. The microfibrous cellulose (MFC) polymers used, however, have a zero or near zero stress-shear rate profile (i.e., zero stress-shear rate slope when plotting shear rate versus stress). One problem associated with zero stress shear rate slope is flow instability and MFC alone will not eliminate this problem. One of the goals of the subject invention is to eliminate such zero stress-shear rate slope, thereby resolving the problem of flow instability.

Fibrous polymer, such as micro fibrous cellulose, has been used, for example, in liquid laundry detergent compositions. WO 2009/135765 (Unilever), for example, discloses a process for making structured liquid detergent composition comprising micro fibrous cellulose. The compositions comprise 25-55% surfactant (we use 15% or less, preferably, 10% or less by wt. in our compositions). There is no disclosure of flow instability (causing product lumpiness, also known as shear banding) or of use of specific polymers to be used in conjunction with MFC to resolve such issue.

WO 2009/101545 (P&G) also discloses liquid detergent compositions comprising micro fibrous cellulose. The reference also discloses typically much higher amounts of surfactant than used in our compositions. Further, compositions of our invention comprise neither enzymes nor chelators/builders, typical ingredients found in laundry detergent compositions.

U.S. 2007/0197779 (CP Kelco) discloses structurant consisting of bacterially product MFC with carboxymethylcellulose and xanthan gum as dispersion aids. Practical difficulties arise when this type of thickener is used with surfactant containing compositions. Microfibrous cellulose, as noted above, will not by itself eliminate the problem of flow instability (associated with zero or near zero stress shear rate slope) in surfactant structured compositions. The compositions are also enzyme-containing detergent liquids.

U.S. Pat. No. 7,776,807 (noted above) discloses liquid cleansing compositions comprising micro fibrous cellulose (MFC). As indicated, rheological properties of the composition include high zero or near zero stress-shear rate slope (associated with flow instability which in turn causes shear banding). Again, fibrous polymers alone do not eliminate zero or near zero rate slope which are particularly a problem in surfactant structured liquid compositions. In such compositions, use of salt to enhance viscosity can result in flow instability and product lumpiness. Applicants seek to protect against flow instability in viscosity ranges from 100 cps to 100,000 cps, preferably 500 to 50,000 cps.

Flow instability or "shear-banding", compared to shear thinning is disclosed generally in "Comparison between Shear Banding and Shear Thinning in Entangled Micellar Solutions", Hu et al., J. Rheol., 2008, 52(2), 379-400; and "Role of Electrostatic Interactions in Shear Banding of Entangled DNA Solutions", Hu et al., Micromolecules, 2008, 41, 6618-6620. Examples A-E of a surfactant system structured with entangled wormlike micelles with and without fibrous polymers, exhibits the undesired flow instability or shear-banding behavior.

Specifically, the phenomenon can be readily observed from compositions having zero or near zero stress-shear rate slope profile measured by standard rheological measurements. FIG. 1 shows typical flow profiles displaying zero stress-shear rate slope for Examples A, C and E. The details of the measurement and instrument are given in the protocol.

From this Figure, it can be seen that there is a zero or near zero slope, for example, in range of 10 to 1000 s$^{-1}$ (shear rate). If stress or force is applied to a liquid composition over this range, a zero-slope curve implies that a single force can have multiple shear rates or flow rates. This is what is meant by "flow instability" and it is such flow instability which causes lumpiness or shear banding.

BRIEF DESCRIPTION OF THE INVENTION

Unexpectedly, applicants have now found that the addition of specific low molecular weight polymer (e.g., relatively low molecular weight, water soluble polymers having molecular weight of from 100 to 1,000,000, preferably 200 to 500,000, more preferably, 250 to 200,000) to compositions comprising fibrous polymer creates a synergistic effect which eliminates flow instability problems observed when fibrous polymer alone is utilized.

More specifically, the invention comprises a liquid composition comprising:

(a) 0.5 to 15% by wt., preferably 1 to 12%, more preferably 1 to 10% by wt. of a surfactant selected from the group consisting of anionic surfactant, nonionic surfactant, amphoteric/zwitterionic surfactant, cationic surfactant and mixtures thereof where said system must comprise at least 1% anionic surfactant (and, preferably, anionic comprises 50% to 100% of said surfactant system);

(b) 0.005 to 2.0%, preferably 0.01 to 1.5%, more preferably 0.01 to 1% of a bacterial cellulose (e.g., microfibrous cellulose); and (c) 0.05 to 3.0%, preferably 0.01 to 2.0%, more preferably 0.5 to 1% of a low molecular, water soluble polymer (e.g., carboxymethylcellulose or linear branched chain polyhydroxyl) having a molecular wt. of 100 to 1,000,000, preferably 200 to 500,000, more preferably 250 to 200,000.

Compositions of the invention (e.g., without shear banding) have slopes of stress versus shear rate in the range of 0.05 to 0.75, preferably 0.08 to 0.6, more preferably 0.1 to 0.5, even more preferably 0.1 to 0.4.

The compositions of the invention contain no enzyme (e.g., type of enzyme typically used in laundry detergent compositions).

In a second embodiment of the invention, the invention relates to a method of eliminating flow instability (which causes shear banding) in liquid composition comprising 0.5 to 15% by wt. surfactant, and 0.005 to 2.0% MFC, which method comprises adding 0.05 to 3% by wt. low molecular weight water soluble polymers to the composition.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental example, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y" it is understood that all ranges combining the different endpoints are also contemplated. Further in specifying the range of concentration, it is noted that any particular upper concentration can be associated with any particular lower concentration. Where the term "comprising" is used in the specification or claims, it is not intended to exclude any terms, steps or features not specifically recited. For the avoidance of doubt, the word "comprising" is intended to mean "including" but not necessarily "consisting of" or "composed of". In other words, the listed steps, options, or alternatives need not be exhaustive. All temperatures are in degrees Celsius (° C.) unless specific otherwise. All measurements are in SI units unless specified otherwise. All documents cited are—in relevant part—incorporated herein by reference.

DETAILED DESCRIPTION OF THE INVENTION

Figure 1:
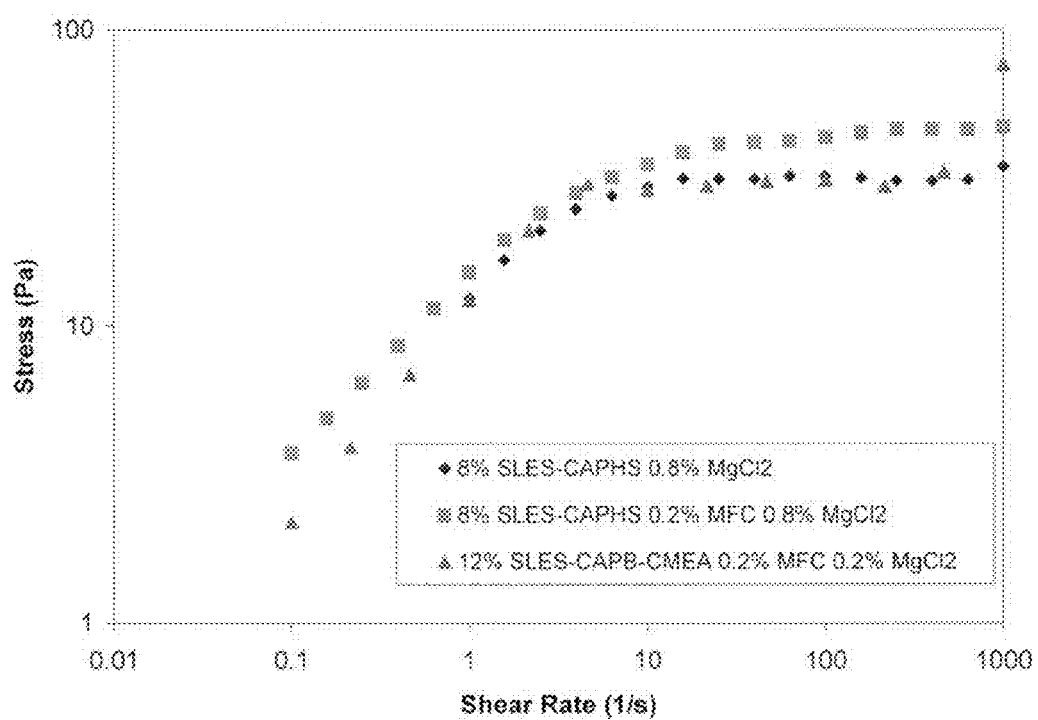
FIG. 1 shows typical flow profiles with zero stress shear rate slope for examples A, C and E. Specifically, applicants have plotted a graph of stress (on y axis, measured in pascals) versus shear rate (on x axis, measured in seconds$^{-1}$) of use of either no (Example A) or 0.2% (Examples C & E) MFC in typical surfactant-structured composition. It is seen that, at shear rate of 10-1000 s$^{-1}$, there is zero or near zero stress-shear rate slope. This implies that a single force will have multiple flow rates flow instability which leads to product lumpiness (also known as shear banding). Measurement of slope is defined in protocol.

The present invention relates to liquid surfactant compositions structured with fibrous polymer (e.g., bacterial cellulose such as microfibrous cellulose or MFC). More specifically, it has been unexpectedly found that when specific low molecular weight water soluble polymers are used in such liquids, the flow instability (causing shear banding) problem associated with the use of fibrous polymer (e.g., MFC) is eliminated.

In a second embodiment, the invention relates to a method of eliminating flow instability in structured liquid surfactant compositions comprising fibrous polymer (e.g., MFC), which method comprises adding specific low molecular weight, water soluble polymer to the composition. These are the same polymers as defined for the first embodiment of the invention.

The first embodiment of the invention comprises a liquid composition comprising:
(a) 0.5 to 15% by wt., preferably 1 to 12%, more preferably 1 to 10% by wt. of a surfactant selected from the group consisting of anionic surfactant, nonionic surfactant, amphoteric/zwitterionic surfactant, cationic surfactant and mixtures thereof where said composition must comprise at least 1% anionic surfactant (and, preferably, anionic comprises 50% to 100% of said surfactant system);
(b) 0.005 to 2.0%, preferably 0.01 to 1.5%, more preferably 0.01 to 1% of a bacterial cellulose (e.g., microfibrous cellulose); and
(c) 0.05 to 3.0%, preferably 0.01 to 2.0%, more preferably 0.5 to 1% of a low molecular, water soluble polymer (e.g., carboxymethylcellulose) having a molecular wt. of 100 to 1,000,000, preferably 200 to 500,000, even more preferably 250 to 200,000.

Compositions of the invention, having noted amounts and type of low molecular weight, water soluble polymers have slope (stress versus shear rate) of from 0.05 to 0.75, preferably 0.08 to 0.6, more preferably 0.1 to 0.5, even more preferably 0.1 to 0.4.

Surfactants

The surfactant can be any of the thousands of anionic surfactants, nonionic surfactants, amphoteric surfactants, zwitterionic surfactants, cationic surfactants and mixtures clearly as are well know in the art.

Anionic surfactants include, but are certainly not limited to aliphatic sulphate, aliphatic sulfonates (e.g., $C_8$ to $C_{22}$ sulfonate or disulfonate), aromatic sulfonates (e.g., alkyl benzene sulfonates), alkyl sulfoccinates, alkyl and acyl taurates, alkyl and acyl sarcosinates, sulfoacetates, alkyl phosphates, carboxylates, isethionates, etc.

Zwitterionic and Amphoteric Surfactants

Zwitterionic surfactants are exemplified by those which can be broadly described as derivatives of aliphatic quaternary ammonium, phosphonium and sulfonium compounds, in which the aliphatic radicals can be straight or branched chain, and wherein one of the aliphatic substituents contains from about 8 to about 18 carbon atoms and one contains an anionioc group, e.g., carboxy, sulfonates, sulfate, phosphate, or phosphonate. A general formula for these compounds is:

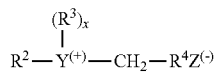

wherein $R^2$ contains an alkyl, alkenyl, or hydroxyl alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is sulfur atom and 2 when Y is nitrogen or phosphorous atom (note that when x is 2, the $R^3$ groups are attached to Y by two different bonds); $R^4$ is an alkylene or hydroxyalkylene of from about 1 to about 4 carbon atoms and Z is a radical selected from the group consisting of carboxylate, sulfonates, sulfate, phosphonate, and phosphate groups.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

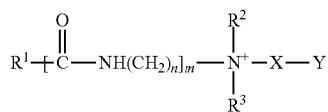

where $R^1$ is alkyl or alkenyl of 7 to 18 carbon atoms;

$R^2$ and $R^3$ are each independently alkyl, hydroxyalkyl or carboxyalkyl or 1 to 3 carbon atoms;

n is 2 to 4;

m is 0 to 1;

X is alkylene of 1 to 3 carbon atoms optionally substituted with hydroxyl, and

Y is $-CO_2-$ or $-SO_3-$

Nonionic Surfactants

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and, ethylenediamine. Other so-called nonionic detergent compounds include long chain tertiary amine oxides, long chain tertiary phosphine oxides and dialkyl sulphoxides.

The nonioinic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

As indicated, surfactant comprises 0.5 to 15%, preferably 1 to 12% by wt. of composition . Further, anionic surfactant must comprise at lest 1% of composition and, preferably, anionic surfactant comprises 50% to 100% of the surfactant system.

Bacterial Cellulose

The external structuring system of the present invention comprises 0.005 to 2.0%, preferably 0.01 to 1.5%, more preferably 0.01 to 1% by wt. bacterial cellulose (e.g., bacterial cellulose network). The term "bacterial cellulose" is intended to encompass any type of cellulose produced via fermentation of bacteria of the genus *Acetobacter* and includes materials referred popularly as microfibrillated cellulose, reticulated bacterial cellulose, and the like.

The bacterial cellulose network may be formed by processing of a mixture of the bacterial cellulose in a hydrophilic solvent, such as water, polyols (e.g., ethylene glycol, glycerin, polyethylene glycol, etc.), or mixtures thereof. This processing is called "activation" and comprises, generally, high pressure homogenization and/or high shear mixing. It has importantly been found that activating the bacterial cellulose under sufficiently intense processing conditions provides for increased yield stress at given levels of bacterial cellulose network. Yield stress is a measure of the force required to initiate flow in a gel-like system. It is believed that yield stress is indicative of the suspension ability of the liquid composition, as well as the ability to remain in situ after application to a vertical surface.

Activation is a process in which the 3-dimensional structure of the bacterial cellulose is modified such that the cellulose imparts functionality to the base solvent or solvent mixture in which the activation occurs, or to a composition to which the activated cellulose is added. Functionality includes providing such properties as shear-thickening, imparting yield stress—suspension properties, freeze-thaw and heat stability, and the like. The processing that is followed during the activation process does significantly more than to just disperse the cellulose in base solvent. Such intense processing "teases apart" the cellulose fibers to expand the cellulose fibers. The activation of the bacterial cellulose expands the cellulose portion to create a bacterial cellulose network, which is a reticulated network of highly intermeshed fibers with a very high surface area. The activated reticulated bacterial cellulose possesses an extremely high surface area that is thought to be at least 200-fold higher than conventional microcrystalline cellulose (i.e., cellulose provided by plant sources). It should be noted that conventional microcrystalline cellulose may still be used.

The bacterial cellulose utilized herein may be of any type associated with the fermentation product of Acetobacter genus microorganisms, and was previously available, for example, from CP Kelco U.S. is CELLULON®. Such aerobic cultured products are characterized by a highly reticulated, branching interconnected network of fibers that are insoluble in water. The preparation of such bacterial cellulose products are well known and typically involve a method for producing reticulated bacterial cellulose aerobically, under agitated culture conditions, using a bacterial strain of *Acetobacter aceti* var. *xylinum*. Use of agitated culture conditions results in sustained production, over an average of 70 hours, of at least 0.1 g/liter per hour of the desired cellulose. Wet cake reticulated cellulose, containing approximately 80-85% water, can be produced using the methods and conditions disclosed in the above-mentioned patents. Dry reticulated bacterial cellulose can be produced using drying techniques, such as spray-drying or freeze-drying, that are well known. See U.S. Pat. Nos. 5,079,162 and 5,144,021.

*Acetobacter* is characteristically a gram-negative, rod shaped bacterium 0.6-0.8 microns by 1.0-4 microns. It is a strictly aerobic organism; that is, metabolism is respiratory, not fermentative. This bacterium is further distinguished by the ability to produce multiple poly β-1,4-glucan chains, chemically identical to cellulose. The microcellulose chains, or microfibers, of reticulated bacterial cellulose are synthesized at the bacterial surface, at sites external to the cell membrane. These microfibers have a cross sectional dimensions of about 1.6 nanometers (nm) to about 3.2 nm by about 5.8 nm to about 133 nm. In one embodiment, the bacterial cellulose network has a widest cross sectional microfiber width of from about 1.6 nm to about 200 nm, alternatively less than about 133 nm, alternatively less than about 100 nm, alternatively less than about 5.8 nm. Additionally, the bacterial cellulose network has an average microfiber length of at least 100 nm, alternatively from about 100 to about 1500 nm. In one embodiment, the bacterial cellulose network has a microfiber aspect ratio, meaning the average microfiber length divided by the widest cross sectional microfiber width, of from about 10:1 to about 1000:1, alternatively from about 100:1 to about 400:1, alternatively from about 200:1 to about 300:1.

The presence of the bacterial cellulose network can be detected by a STEM micrograph imaging. A liquid detergent composition sample is obtained. A 1500 mesh copper TEM grid is placed on filter paper and 15 drops of the sample are applied to the TEM grid. The TEM grid is transferred to fresh filter paper and rinsed with 15 drops of deionized water. The TEM grid is then imaged in a S-5200 STEM micrograph instrument to observe for a fibrous network. Those of skill in the art will understand that if a fibrous network is detected, the cross dimensional of the fibers as well as the aspect ratio can be determined. Those of skill in the art will also recognized that alternative analytic techniques can be used to detect the presence of the bacterial cellulose network such as Atomic Force Microscopy using the same TEM grid and deposition and rinsing steps as disclosed above. An Atomic Force Microscopy 3D representation can be obtained showing the fiber dimensions as well as degree of networking.

The small cross sectional size of these *Acetobacter*-produced fibers, together with the large length and the inherent hydrophilicity of cellulose, provides a cellulose product having an unusually high capacity for absorbing aqueous solutions. Additives have often been used in combination with the bacterial cellulose to aid in the formation of stable, viscous dispersions.

Non-limiting examples of additional suitable bacterial celluloses are disclosed in and U.S. Pat. No. 6,967,027 to Heux et al; U.S. Pat. No. 5,207,826 to Westland et al; U.S. Pat. No. 4,487,634 to Turbak et al; U.S. Pat. No. 4,373,702 to Turbak et al and U.S. Pat. No. 4,863,565 to Johnson et al, U.S. Pat. Publication No. 2007/0027108 to Yang et al.

Methods of Activating the Bacterial Cellulose

In one embodiment, the bacterial cellulose network is formed by activating the bacterial cellulose under intense high shear processing conditions. Intense high shear processing conditions can provide the bacterial cellulose network with enhanced structuring capabilities. By using intense processing conditions, the bacterial cellulose network can provide the desired structuring benefits at lower levels and without a need for costly chemical and physical modifications.

In one embodiment, the step of activating said bacterial cellulose under intense high shear processing conditions comprises: activating the bacterial cellulose and a solvent, e.g. water, at an energy density above about $1.0 \times 10^6$ J/m$^3$, alternatively above than $2.0 \times 10^6$ J/m$^3$. In one embodiment, the step of activation is performed with an energy density from $2.0 \times 10^6$ J/m$^3$ to about $5.0 \times 10^7$ J/m$^3$, alternatively from about $5.0 \times 10^6$ J/m$^3$ to about $2.0 \times 10^7$ J/m$^3$, alternatively from about $8.0 \times 10^6$ J/m$^3$ to about $1.0 \times 10^7$ J/m$^3$. By activating the bacterial cellulose under intense high shear processing conditions as set forth herein, formulations having even below 0.05 wt. % of said bacterial cellulose are capable of the desired rheological benefits such as yield stress and particle suspension. In one embodiment, where activation is performed via intense high shear processing, the level of bacterial cellulose is from 0.005 wt. % to about 0.05 wt. %, alternatively below about 0.03 wt. %, alternatively below about 0.01 wt. %.

Processing techniques capable of providing this amount of energy density include conventional high shear mixers, static mixers, prop and in-tank mixers, rotor-stator mixers, and Gaulin homogenizers, and SONOLATOR® from Sonic Corp. of CT.

In one embodiment, the step of activating said bacterial cellulose under intense high shear processing conditions involves causing hydrodynamic cavitation is achieved using a SONOLATOR®.

Certain processing conditions enhance the ability of the bacterial cellulose to provide desired rheological benefits, including enhanced yield stress at lower levels of the bacterial cellulose. Without intending to be bound by theory, this benefit is believed to be achieved by increasing the interconnectivity of the bacterial cellulose network formed within the liquid matrix.

One method to enhance the ability of a bacterial cellulose to form the bacterial cellulose network is to activate the bacterial cellulose with an aqueous solution as a premix under conventional mixing conditions prior to be placed in contact with a second stream. A second stream can be provided comprising the other desired components, such as the surfactants, perfumes, particles, adjunct ingredients, etc. In one embodiment, the bacterial cellulose and an aqueous solution are combined as a premix. This premix can be subjected to intense high shear conditions but need not be. In one embodiment, it is desired to perform this premix step using conventional mixing technologies such as a batch, or continuous in line mixer at energy densities up to about $1.0 \times 10^6$ J/m$^3$.

Another method to enhance the ability of the bacterial cellulose to form the bacterial cellulose network is to contact the bacterial cellulose in dry or powder form directly into a feed stream of the liquid actives into the mixing chamber of an ultrasonic homogenizer or in line mixer. The powder can be added immediately before the feed(s) enter the mixing chamber or can be added as a separate feed from the active feed stream. Advantageously, by introducing the powder form without premixing or having a separate activation step, a single pass system can be achieved which allows for processing simplicity and cost/space savings.

Polymeric Thickened Coated Bacterial Cellulose

In one embodiment, the external structuring system further comprises a bacterial cellulose which is at least partially coated with a polymeric thickener. This at least partially coated bacterial cellulose can be prepared in accordance with the methods disclosed in U.S. Pat. Publication No. 2007/0027108 to Yang et al. at paragraphs 8-19. In one suitable process, the bacterial cellulose is subjected to mixing with a polymeric thickener to at least partially coat the bacterial cellulose fibers and bundles. It is believed that the commingling of the bacterial cellulose and the polymeric thickener allows for the desired generation of a polymeric thickener coating on at least a portion of the bacterial cellulose fibers and/or bundles.

Low Molecular Weight Polymer

A third required component of the invention is the low molecular weight, water soluble polymers. These polymers synergistically interact with MFC to ensure that flow instability (which would be found in absence of use of such polymers) is eliminated.

Typically, such polymers may be polyols which include linear and branched chain alkyl polyhydroxyl compounds such as, for example, alkylene glycol (e.g., propylene glycol), sorbitol or glycerin having molecular weight (e.g., weight average molecular weight) of from about 100 to 150,000, preferably 200 to 100,000, more preferably 250 to 50,000. Also polymeric polyols such polypropylene glycol, polyethylene glycol, butylene glycol (all of MW 100 to 150,000) may be used.

Another example of low molecular weight, water soluble polymers include low molecular weight water soluble gums, for example, carboxymethyl cellulose, wherein such gums have molecular weight of from about 100 to 1,000,000, preferably 500 to 500,000, more preferably 1,000 to 150,000. Typically, gums include carbohydrate gums such as cellulose gum, microcrystalline cellulose, cellulose gel, hydroxyethyl cellulose, hydroxypropyl cellulose, sodium carboxymethy cellulose, hydroxymethyl carboxymethyl cellulose, carrageenan, methyl cellulose, ethyl cellulose, guar gum, gum Karaya, gum tragecanth, gum arabic, gum acacia, gum agar and xanthan gum. Preferred gums are cellulose gums and xanthan gum when polymers include polyacrylamides and polyvinyl pyrollidone.

Other polymers which may be used include acrylates, acrylate copolymers, starches, polyacrylamides and polyvinyl pyrrolidone.

In a preferred embodiment of the invention, the polymer is a polyol as noted above of MW 100 to 150,000 or carboxymethyl cellulose of MW 500 to 500,000.

By water soluble is meant that a 3% solution of the polymer in water will be soluble in water.

The polymers comprise 0.05 to 3.0%, preferably 0.1 to 2.0% by wt. of the composition.

Typically, the compositions containing surfactant, bacterial cellulose and low molecular weight polymer as noted above are low surfactant, liquid aqueous cleansers. Typically, compositions comprise 60-95% water, have pH of 5-8 and viscosity 100-100,000 centipoise (cps).

The compositions may contain organic or inorganic stabilizers.

The composition also comprises other ingredients typically found in liquid formulations.

Among these are included auxiliary thickeners, perfumes, sequestering agents (e.g., ethyl diamine tetra acetate, known as EDTA); cooling agents; opacifiers and pearlizers (e.g., zinc or magnesium, stearate, titanium dioxide).

Other optional ingredients include antimicrobial agents; preservatives (e.g., parabens, sorbic acid); suds booster (e.g., coconut acyl mono- or diethanolamide); antioxidants; cationic conditioners (e.g., Merquat® and Jaguar® type conditioners); exfoliants; ionizing salts; organic acids (e.g., citric or lactic acid).

PROTOCOL AND EXAMPLES

Measurement of Stress (Pa) Versus Shear Rate (Seconds$^{-1}$)

Rheological measurements were done on Paar Physical stress controlled rheometer (MCR-300). To determine the stress-shear rate slope profile (correlated with flow instability and consequent shear banding), experiments were performed in rate sweep mode from shear rates of 0.1-1000 1/s using cone and plate geometry with 50 mm diameter and 2° cone angle. For low-shear viscosity, experiments were conducted in shear rate sweep mode from shear rates of 10 to $10^{-6}$ reciprocal seconds. Graphs were obtained by plotting stress (Pascals) against shear rate.

Measurement of Slope Value

Slope, n, is obtained by fitting stress values for shear rates between 10 and 1,000 (the slope measured through these values also may be referenced to as the "second slope" compared to "first slope" found at lower shear rates; and further may be referred to as "flat region" of the stress versus shear rate slope) using a power law equation given by:

$$\tau \alpha \gamma^n$$

where 96 is the stress, γ is the shear rate and n is the powerlaw index (also referred to as the slope).

Examples 1-9 and Comparatives A-E

In order to show the effect of specific low molecular weight, water soluble polymers in the elimination of flow instability, applicants set forth Table 1 (Comparatives A-E) and Table 2 (Examples 1-9) as noted below.

TABLE 1

| Chemical Component | A | B | C | D | E |
|---|---|---|---|---|---|
| SLES-1EO (70%) | 5.5 | 5.5 | 5.5 | 9 | 9 |
| Cocamido propylhydroxy sultaine—(CAPHS) | 2.5 | 2.5 | 2.5 | | |
| CAPB | | | | 2 | 2 |
| CMEA | | | | 1 | 1 |
| MFC (1%) | 0 | 0.1 | 0.2 | 0.1 | 0.2 |
| Perfume | 1 | 1 | 1 | 1 | 1 |
| Methyl-chloroisothiazolinone Methylisothiazolinone | 0.0003 | 0.0003 | 0.0003 | 0.0003 | 0.0003 |
| Tetrassodium EDTA | 0.05 | 0.05 | 0.05 | 0.05 | 0.05 |
| Etidronic acid | 0.02 | 0.02 | 0.02 | 0.02 | 0.02 |
| Cekol 10000 | — | — | — | — | — |
| Water | to 100 | to 100 | to 100 | to 100 | to 100 |
| MgCl2 | 0.8 | 0.8 | 0.8 | 0.2 | 0.2 |
| pH | 7 | 7 | 7 | 7 | 7 |

SLES - 1EO = sodium lauryl ether sulphate with 1 ethylene oxide group ethoxylation
CAPB—cocoamidopropyl betaine
CMEA—cocomonoethanolamide
MFC = microfibrous cellulose (bacterial)
Cekol ® 10,000 is carboxymethyl cellulose gum of MW 10,000 (100 to 1,000,000, preferably 250 to 200,000)

TABLE 2

| Component | 1 | 2 | 3 | 4 | 5 | 6 | 7 | 8 | 9 |
|---|---|---|---|---|---|---|---|---|---|
| SLES-1EO (70%) | 5.5 | 5.5 | 5.5 | 5.5 | 5.5 | 5.5 | 5.5 | 5.5 | 5.5 |
| Cocamido propylhydroxy sultaine-CAPHS | 2.5 | 2.5 | 2.5 | | | 2.5 | 2.5 | 2.5 | 2.5 |
| CAPB | | | | 2.5 | 2.5 | | | | |

TABLE 2-continued

| Component | 1 | 2 | 3 | 4 | 5 | 6 | 7 | 8 | 9 |
|---|---|---|---|---|---|---|---|---|---|
| CMEA | | | | | 1 | | | | |
| Sodium cocoyl glycinate[1] | | | | | | 1 | | | |
| MFC (1%) | 0.1 | 0.1 | 0.2 | 0.2 | 0.2 | 0.2 | 0.2 | 0.2 | 0.2 |
| Cekol 10000 | 1.5 | 1.5 | 1.5 | 1.5 | 1.5 | 1.5 | | | |
| Cekol 2000 | | | | | | | 1.5 | 1.5 | |
| Cekol 100000 | | | | | | | | | 1.5 |
| Glycerine | 5 | 5 | | 5 | 5 | 5 | | | |
| Perfume | 1 | 1 | 1 | 1 | 1 | 1 | 1 | 1 | 1 |
| Methylchloroisothiazolinone Methylisothiazolinone | 0.0003 | 0.0003 | 0.0003 | 0.0003 | 0.0003 | 0.0003 | 0.0003 | 0.0003 | 0.0003 |
| Tetrassodium EDTA | 0.05 | 0.05 | 0.05 | 0.05 | 0.05 | 0.05 | 0.05 | 0.05 | 0.05 |
| Etidronic Acid | 0.02 | 0.02 | 0.02 | 0.02 | 0.02 | 0.02 | 0.02 | 0.02 | 0.02 |
| Water | to 100 | to 100 | to 100 | to 100 | to 100 | to 100 | to 100 | to 100 | to 100 |
| MgCl2 | 0 | 0.8 | 0.3 | 0.3 | 0.3 | 0.3 | 0.8 | 0.3 | 0.3 |
| pH | 7 | 7 | 7 | 7 | 7 | 7 | 7 | 7 | 7 |

[1]Sodium salt of acyl group, e.g., $R\overset{O}{\underset{\|}{C}}$, where R is $C_8$ to $C_{24}$, and glycine.

Table 1 is a surfactant composition containing 0 (Example A) to 0.2% (Examples B to E) MFC. Three of the examples (A, C, E) were plotted to yield profiles of stress (Pa) versus shear rate (1/s) as set forth in FIG. 1.

As seen from FIG. 1, the slope of stress versus shear rate at, for example, 10 to 1000 $s^{-1}$ was zero or near zero (0.025). In such compositions, a single force can have multiple shear rate or flow rates. This is known as flow instability and is associated with product lumping or shear banding.

Figure 2:
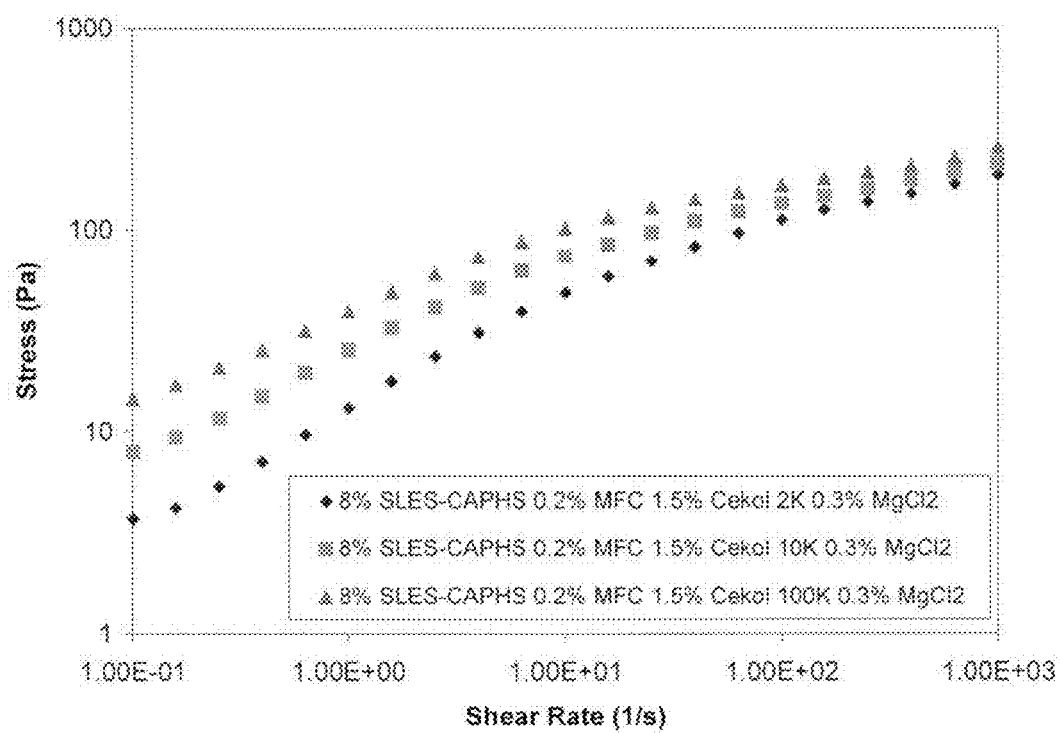
FIG. 2 shows some typical flow profile for examples 6, 8 and 9 in the Examples. Here it is seen that when specific low molecular wt. water soluble polymers are used with MFC, the stress-shear rate slope increases from 0.025 (when no polymer is used) to 0.2 and 0.3 for polymers with molecular weight of 100,000 and 2,000, respectively (slope increase being correlated with less flow instability). Since slope increases with lower molecular weight polymers more so than with higher (e.g., Cekol® 2K versus Cekol® 100K), this suggest that high molecular weight polymers (e.g., above 1,000,000) do not eliminate flow instability. Preference range for eliminating flow instability is polymers with molecular weight of 100 to 1,000,000, preferably 200 to 500,000.

When low molecular weight, water soluble polymer (carboxymethylcellulose of MW 2000 to 100,000; see Table 2, Examples 1-9) was added to the compositions, results for examples 1, 8 and 9 was plotted in FIG. 2. As seen from FIG. 2, the slope was significantly increased to 0.2 or 0.3 in the specific examples (use of low molecular weight polymers of invention increases slope from 0.025 slope of compositions without polymer to slopes of 0.05 to 0.75, preferably 0.08 to 0.6, more preferably 0.1 to 0.5). Compositions with slope in this above-noted range are associated with elimination of flow instability and resulting resolution of lumpiness or shear banding problem.

What can also be seen is that the lower MW polymers (e.g., carboxymethylcellulose of MW 200 versus 100,000) were better at increasing slope over desired shear rate range. Since smaller slopes are indicative of lumpiness and flow instability, such lower MW polymers (which increase slope) are thus preferred.

The invention claimed is:

1. A liquid surfactant composition comprising:
   (a) 0.5 to 15% by wt., preferably 1 to 12%, more preferably 1 to 10% by wt, of a surfactant selected from the group consisting of anionic surfactant, nonionic surfactant, amphoteric/zwitterionic surfactant, cationic surfactant and mixtures thereof where said system must comprise at least 1% anionic surfactant;
   (b) 0.005 to 2.0% by wt. bacterial cellulose used to structure said composition and wherein said cellose has been subject to high shear processing at energy density above $1.0 \times 10^6$ J/m$^3$; and
   (c) 0.1 to 3.0% by wt., carboxymethylcellulose having a molecular wt. of 1,000 to 150,000 added to the composition.

2. A composition according to claim 1, wherein anionic surfactant comprises 50% to 100% of the surfactant of (a).

3. A composition according to claim 1, wherein said bacterial cellulose is microfibrous cellulose.

4. A composition according to claim 1 comprising 0.01 to 1.5% bacterial cellulose.

5. A composition according to claim 1, wherein composition has slope of stress (on y axis, measured in pascals) versus shear rate (on x axis, measured in $s^{-1}$) of 0.05 to 0.75.

* * * * *